(12) United States Patent
Leroux et al.

(10) Patent No.: US 10,596,114 B2
(45) Date of Patent: Mar. 24, 2020

(54) LIPOSOME COMPOSITION FOR USE IN PERITONEAL DIALYSIS

(71) Applicant: ETH ZURICH, Zurich (CH)

(72) Inventors: Jean-Christophe Leroux, Zurich (CH); Vincent Forster, Zurich (CH)

(73) Assignee: ETH ZURICH, Zurich (CH)

( * ) Notice: Subject to any disclaimer, the term of this patent is extended or adjusted under 35 U.S.C. 154(b) by 0 days.

(21) Appl. No.: 14/420,654

(22) PCT Filed: Aug. 6, 2013

(86) PCT No.: PCT/EP2013/002352
§ 371 (c)(1),
(2) Date: Feb. 9, 2015

(87) PCT Pub. No.: WO2014/023421
PCT Pub. Date: Feb. 13, 2014

(65) Prior Publication Data
US 2015/0216802 A1    Aug. 6, 2015

(30) Foreign Application Priority Data
Aug. 9, 2012   (EP) .................................. 12005796.3

(51) Int. Cl.
*A61K 9/127*   (2006.01)
*A61M 1/28*    (2006.01)

(52) U.S. Cl.
CPC ............ *A61K 9/127* (2013.01); *A61K 9/1271* (2013.01); *A61M 1/287* (2013.01); *A61K 9/1272* (2013.01); *A61K 9/1273* (2013.01)

(58) Field of Classification Search
None
See application file for complete search history.

(56) References Cited

U.S. PATENT DOCUMENTS

| | | | | |
|---|---|---|---|---|
| 5,744,158 A | * | 4/1998 | Mayer ..................... | A61K 9/127 424/450 |
| 5,843,474 A | * | 12/1998 | Williams ................ | A61K 9/127 424/450 |
| 2004/0208922 A1 | | 10/2004 | Mehlhorn | |
| 2008/0096185 A1 | | 4/2008 | Putz et al. | |

FOREIGN PATENT DOCUMENTS

| GB | 2013523 B | 10/1982 |
|---|---|---|
| JP | S54121000 A | 9/1979 |

OTHER PUBLICATIONS

Antimisiaris et al, "Liposomes and Drug Delivery," Pharmaceutical Sciences Encyclopedia, pp. 1-91 (2010).*
DiZerega et al, "Peritoneal Fluid," The Peritoneum, Springer-Verlag, pp. 26-56 (Year: 1992).*
International Search Report and Written Opinion of the International Searching Authority, for PCT/EP2013/002352, dated Sep. 25, 2013.
Forster, et al., "Treatment of calcium channel blocker-induced cardiovascular toxicity with drug scavenging liposomes", Biomaterials, vol. 33, No. 13, Feb. 11, 2012, pp. 3578-3585, XP028461961, DOI: 10.1016/J.Biomaterials.2012.01.042.
Stein, et al., "Cholesterol removal by peritoneal lavage with phospholipid-HDL apoprotein mixtures in hypercholesterolemic hamster", Biochimica ET Biophysica ACTA—Lipids and Lipid Metabolism, vol. 1006, No. 1, Nov. 1989, pp. 144-146, XP027222744; ISSN:0005-2760.
Arbeiter, A.K., et al., "Continuous Venovenous Haemodialysis (CVVHD) and Continuous Peritoneal Dialysis (CPD) in the Acute Management of 21 Children With Inborn Errors of Metabolism," Nephrology, Dialysis, Transplantation 25(4):1257-1265, Oxford University Press, England (Apr. 2010).
Auron, A. and Brophy, P.D., "Hyperammonemia in Review: Pathophysiology, Diagnosis, and Treatment," Pediatric Nephrology 27(2):207-222, Springer International, Germany (Feb. 2012).
Bertrand, N., et al., "Transmembrane pH-gradient Liposomes to Treat Cardiovascular Drug Intoxication," ACS Nano 4(12):7552-7558, American Chemical Society, United States (Dec. 2010).
Bitounis, D., et al., "Optimizing Druggability through Liposomal Formulations: New Approaches to an Old Concept," ISRN Pharmaceutics 2012:11 pages, Hindawi Pub. Corp., Egypt (2012).
Cave, G. and Harvey, M., "Intravenous Lipid Emulsion as Antidote Beyond Local Anesthetic Toxicity: A Systematic Review," Academic Emergency Medicine 16(9):815-824, Wiley, United States (Sep. 2009).
Clay, A.S. and Hainline, B.E., "Hyperammonemia in the ICU," Chest 132(4):1368-1378, Elsevier, United States (Oct. 2007).
Dadashzadeh, S., et al., "Peritoneal Retention of Liposomes: Effects of Lipid Composition, Peg Coating and Liposome Charge," Journal of Controlled Release 148(2):177-186, Elsevier Science Publishers, Netherlands (Dec. 2010).
Fenske and Cullis, "Encapsulation of Drugs within Liposomes by pH-Gradient Techniques, Liposome Technology," vol. II, Edited by Gregory Gregoriadis, Informa Healthcare pp. 27-50 (Sep. 2006).
Harvey, M., et al., "Correlation of Plasma and Peritoneal Diasylate Clomipramine Concentration With Hemodynamic Recovery After Intralipid Infusion in Rabbits," Academic Emergency Medicine 16(2):151-156, Wiley, United States (Feb. 2009).

(Continued)

*Primary Examiner* — Dennis J Parad
(74) *Attorney, Agent, or Firm* — Sterne, Kessler, Golstein & Fox P.L.L.C.

(57) ABSTRACT

The present invention is directed to a liposome composition for use in the peritoneal dialysis of patients suffering from endogenous or exogenous toxicopathies, wherein the pH within the liposomes differs from the pH in the intraperitoneal cavity and wherein the pH within the liposome results in a liposome-encapsulated charged toxin. The invention also relates to a pharmaceutical composition comprising said liposomes. A further aspect of the present invention relates to a method of treating patients suffering from endogenous or exogenous toxicopathies, preferably selected from drug, metabolite, pesticide, insecticide, toxin, and chemical warfare toxicopathies, more preferably hyperammonemia, comprising the step of administering liposomes of the invention in a therapeutically effective amount into the peritoneal space of a patient in need thereof. Next to human, the present invention is particularly suitable to veterinary aspects.

28 Claims, 3 Drawing Sheets

(56) References Cited

OTHER PUBLICATIONS

Hirano, K. and Hunt, C.A., "Lymphatic Transport of Liposome-encapsulated Agents: Effects of Liposome Size Following Intraperitoneal Administration," Journal of Pharmaceutical Sciences 74(9):915-921, Elsevier, United States (Sep. 1985).

Hope, M.J., et al., "Production of Large Unilamellar Vesicles by a Rapid Extrusion Procedure: Characterization of Size Distribution, Trapped Volume and Ability to Maintain a Membrane Potential," Biochimica et Biophysica Acta 812(1):55-65, Elsevier Pub. Co., Netherlands (Jan. 1985).

Jamaty, C., et al., "Lipid Emulsions in the Treatment of Acute Poisoning: A Systematic Review of Human and Animal Studies," Clinical Toxicology 48(1):1-27, Taylor & Francis, England (Jan. 2010).

Leroux, J.C., "Injectable Nanocarriers for Biodetoxification," Nature Nanotechnology 2(11):679-684, Nature Pub. Group, England (Nov. 2007).

Lining, M., "Renal Failure," The Fourth Military Medical University Press, 1st edition, p. 281 (Apr. 2007).

Madden, T.D., et al., "The Accumulation of Drugs Within Large Unilamellar Vesicles Exhibiting a Proton Gradient: A Survey," Chemistry and Physics of Lipids 53(1):37-46, Elsevier Science Ireland Ltd, Ireland (Mar. 1990).

Mayer, L.D., et al., "Uptake of Adriamycin Into Large Unilamellar Vesicles in Response to a pH Gradient," Biochimica et Biophysica Acta 857(1):123-126, Elsevier Pub. Co., Netherlands (May 1986).

Mirahmadi, M., et al., "Effect of Liposome Size on Peritoneal Retention and Organ Distribution After Intraperitoneal Injection in Mice," International Journal of Pharmaceutics 383(1-2):7-13, Elsevier/North-Holland Biomedical Press, Netherlands (Jan. 2010).

Parker, R.J., et al., "Lymphatic Absorption and Tissue Disposition of Liposome-entrapped [14C]adriamycin Following Intraperitoneal Administration to Rats," Cancer Research 41(4):1311-1317, American Association for Cancer Research, United States (Apr. 1981).

Pela, I., et al., "Peritoneal Dialysis in Neonates With Inborn Errors of Metabolism: Is It Really Out of Date?," Pediatric Nephrology 23(1):163-168, Springer International, Germany (Jan. 2008).

Sadzuka, Y., et al., "Intraperitoneal Administration of Doxorubicin Encapsulating Liposomes Against Peritoneal Dissemination," Toxicology Letters 116(1-2):51-59, Elsevier, Netherlands (Jul. 2000).

Verschraegen, C.F., et al., "Phase I Clinical and Pharmacological Study of Intraperitoneal Cis-bis-neodecanoato(trans-R, R-1, 2-diaminocyclohexane)-platinum II Entrapped in Multilamellar Liposome Vesicles," Journal of Cancer Research and Clinical Oncology 129(10):549-555, Springer-Verlag, Germany (Oct. 2003).

Cutler; R.E. et al., "Extracorporeal removal of drugs and poisons by hemodialysis and hemoperfusion," Ann. Rev. Pharmacol. Toxicol. 27:169-91, Annual Review, United States (1987).

Dizerega; G.S. et al., "Peritoneal Fluid," in *The Peritoneum*, pp. 26-56, Springer-Verlag, Germany (1992).

Donn; S.M. et al., "Comparison of exchange transfusion, peritoneal dialysis, and hemodialysis for the treatment of hyperammonemia in an anuric newborn infant," Journal of Pediatrics 95(1):67-70, Elsevier, Netherlands (1979).

Fertel; B.S. et al., "Extracorporeal Removal Techniques for the Poisoned Patient: A Review for the Intensivist," Journal of Intensive Care Medicine 25(3):139-48, Sage Publications, England (2010).

Foster; V. et al., "Liposome-supported peritoneal dialysis for detoxification of drugs and endogenous metabolites," Sci. Transl. Med. 6(258ra141):1-9, AAAS, United States (2014).

Garlich; F.M. et al., "Have Advances in Extracorporeal Removal Techniques Changed the Indications for Their Use in Poisonings?" Advances in Chronic Kidney Disease 18(3):172-9, Elsevier, Netherlands (2011).

Ghannoum; M. et al., "Enhanced Poison Elimination in Critical Care," Advances in Chronic Kidney Disease 20(1):91-101, Elsevier, Netherlands (2013).

Haberle; J. et al., "Suggested guidelines for the diagnosis and management of urea cycle disorders," Orphanet Journal of Rare Diseases 7:32, BioMed Central, England (2012).

Keyvan-Larijarni; H. et al., "Methanol Intoxication: Comparison of Peritoneal Dialysis and Hemodialysis Treatment," Arch Intern Med 134:293-6, American Medical Association, United States (1974).

Lubis; H.R. et al., "Extracorporeal Methods in the Treatment of Poisoning," Acta Med. Indones.-Indones. J. Intern. Med. 40(2):84-8, The Indonesian Society of Internal Medicine, Indonesia (2008).

Winchester; J.F. et al., "Treatment of Poisoning with Extracorporeal Methods," in *Handbook of Dialysis Therapy*, 4th ed. Nissenson A.R. and Fine R.N., Elsevier, Netherlands (2008).

Winchester; J.F. and Harbord; N.B., "Intoxications Amenable to Extracorporeal Removal," Advances in Chronic Kidney Disease 18(3):167-71, National Kidney Foundation (2011).

* cited by examiner

LIPOSOME COMPOSITION FOR USE IN PERITONEAL DIALYSIS

CROSS-REFERENCE TO RELATED APPLICATIONS

The present disclosure is entitled to the benefit under 35 U.S.C. § 120 and 365(c) of International Patent Application PCT/EP2013/002352, entitled, "Liposome Composition for Use in Peritoneal Dialysis", filed, 6 Aug. 2013, which claims priority to European Patent Application 12005796.3, filed, 9 Aug. 2012, which are incorporated herein by reference in their entirety.

FIELD OF THE INVENTION

The present invention is directed to a liposome composition for use in the peritoneal dialysis of patients suffering from endogenous or exogenous toxicopathies, wherein the pH within the liposomes differs from the pH in the peritoneal cavity and wherein the pH within the liposome results in a liposome-encapsulated charged toxin. The invention also relates to a pharmaceutical composition comprising said liposomes. A further aspect of the present invention relates to a method of treating patients suffering from endogenous or exogenous toxicopathies, preferably selected from drug, metabolite, pesticide, insecticide, toxin, and chemical warfare toxicopathies, more preferably hyperammonemia, comprising the step of administering liposomes of the invention in a therapeutically effective amount into the peritoneal space of a patient in need thereof. Next to human, the present invention is particularly suitable to veterinary aspects.

BACKGROUND OF THE INVENTION

In order to alter the pharmacokinetic and biodistribution properties of drugs, a variety of lipid- and polymer-based particles have been developed and characterized that include liposomes, i.e. small lipid bilayer particles with a diameter in the nanometer to micrometer size range, wherein the lipid bilayer surrounds an aqueous environment on the inside. Liposomes are presently used in medicine for drug delivery and in research for drug detoxification.

Drugs can be encapsulated in liposomes by a number of techniques, e.g. by passive methods and pH-gradient techniques. For a review see Fenske and Cullis, Encapsulation of Drugs within Liposomes by pH-Gradient Techniques, Liposome Technology, Volume II, Edited by Gregory Gregoriadis, Informa Healthcare September 2006, 27-50. The advantage of a pH gradient across the lipid bilayer is that once the drug is inside, it can be charged by protonation or deprotonation depending on the drug and the pH, so that its back transfer through the lipophilic membrane to the outside is hindered. See for example Mayer et al., Biochimica et Biophysica Acta, 857:123-126, 1986 and Madden et al., Chemistry and Physics of Lipids, 53:37-46, 1990. Therefore, liposomal carrier systems can significantly buffer the toxicity of drugs by entrapping them in their lumen. Liposomal drugs are regularly administered intravenously or at the site of intended drug action, e.g. intraperitoneally. For intraperitoneal liposome drug delivery, reference is made, for example, to Verschraegen et al., J. Cancer Res. Clin. Oncol., 129:549-555, 2003 and Parker et al., Cancer Res. 41: 1311-1317, 1981. Peritoneal retention of intraperitoneally administered liposomally entrapped drugs depends on the composition of the formulation, for example, the lipid composition of the lipid bilayer, the amount of cholesterol included, the size of the liposome, the charge of the liposome, and/or the coating of the liposome, e.g. with PEG (polyethylene glycol). Intraperitoneally administered liposomal drugs are subject to blood and lymphatic transport and can be detected in blood, lymph nodes as well as in a number of organs. In particular the size of liposomes has an influence on peritoneal retention. For intravenously injected liposomes, a diameter of about 100 nm is often considered as optimal for prolonged blood circulation, whereas increasing liposome size produces higher peritoneal retention when injected intraperitoneally. Liposomes having a size of about 1000 nm or greater have the highest peritoneal cavity retention. For further information on factors influencing the peritoneal retention of intraperitoneally administered liposomes, reference is made to, for example, Sadzuka et al., Toxicology Letters 116:51-59, 2000; Dadashzadeh et al., Journal of Controlled Release, 148:177-186, 2010; Mirahmadhi et al., International Journal of Pharmaceutics, 383:7-13, 2010; Hirano and Hunt, Journal of Pharmaceutical Sciences, 74 (9), 915-921, 1985.

Moreover, liposomes as well as lipids in emulsion have utility in drug detoxification.

Jamaty et al., Clinical Toxicology 48:1-27, 2010 review the literature on the use of intravenous fat emulsions (IFE), i.e. lipid emulsions in the treatment of acute drug poisoning. Intralipid® is a brand name for a clinically relevant commercial fat emulsion comprising 10, 20 or 30% by weight of purified soy bean oil as well as purified egg phospholipids, glycerin and water for intravenously or parenterally administered nutrition in case of malnourishment. Moreover, it has utility as vehicle for the anesthetic drugs propofol and etomidate as well as for treating severe cardiotoxicity caused by overdose of local anaesthetic drugs such as bupivacaine to save patients otherwise unresponsive to common resuscitation methods. For nutritional and antidote therapy, Intralipid® is administered intravenously. Cave and Harvey (Academic Emergency Medicine, 16:151-156, 2009) reviewed the literature on the use of IFE in antidote therapy. And in an animal model of clomipramine infusion-treated rabbits, Intralipid® administered intravenously and concomitantly by peritoneal administration showed an enhanced clomipramine extraction over intravenous administration of Intralipid® alone (see Harvey et al., Academic Emergency Medicine, 16:815-824, 2009). The antidote mechanism underlying IFE is that the lipid formulation scavenges and thereby masks the toxic drug by lipid extraction. Of course, this mechanism is only available for drugs with sufficient lipophilicity and depends on the extraction coefficient of the drug in the lipid composition.

Like IFE, intravenously administered liposomes are investigated to treat cardiovascular drug intoxication. J.-C. Leroux, Nature Biotechnology, 2:679-864, 2007, reviews the use of injectable nanocarriers, in particular of liposomes for drug detoxification. Bertrand et al., ACS Nano, 4 (12), 7552-7558, 2010 demonstrated a detoxification with intravenously administered, transmembrane, pH-gradient liposomes in rats receiving intravenous bolus of or perfusion with diltiazem, a cardiovascular drug. Unlike the lipid extraction with IFE the liposomal mechanism of action is the liposomal uptake and charging of the drug by the pH gradient to make the uptake irreversible. Compared to IFE, drug scavenging liposomes are much more efficient in capturing drugs, in particular calcium channel blockers, see for example, Forster et al., Biomaterials 33, 3578-3585, 2012.

Hyperammonemia refers to a clinical condition associated with elevated ammonia levels manifested by a variety of symptoms including central nervous system (CNS) abnormalities. When present in high concentration ammonia is toxic. Endogenous ammonia intoxication can occur when there is an impaired capacity of the body to excrete nitrogenous waste, as seen with congenital enzymatic deficiencies. A variety of environmental causes and medications may also lead to ammonia toxicity. For a review of ammonemia reference is made to Auron and Brophy, Pediatr. Nephrol., 27:207-222, 2012; and Clay and Hainline, CHEST, Official journal of the American College of Chest Physicians, (132), 1368-1378, 2007. Usually, hyperammonemia is associated with cerebral edema, decreased cerebral metabolism and increased cerebral blood flow. Next to therapies that treat intracranial hypertension, nutritional support to prevent protein catabolism and stopping nutritional intake of protein, it may be necessary to reduce ammonia levels by actively removing ammonia. Besides nitrogen elimination through pharmacological manipulation, e.g. administration of sodium phenylacetate and sodium benzoate, to promote the clearance of ammonia through "alternative" metabolic pathways, peritoneal dialysis, hemodialysis, continuous venovenous hemofiltration, continuous venovenous hemodiafiltration and continuous arteriovenous hemodiafiltration are effective ways of removing ammonia and have been helpful in treating hyperammonemia associated with urea cycle disorders in children and adults. In particular for children with inborn metabolism errors venovenous haemodialysis and continuous peritoneal dialysis are a treatment of choice for the acute management of hyperammonemia, e.g. see Arbeiter et al., Nephrol. Dial. Transplant., 25:1257-1265, 2010 and Pela et al.; Pediatr. Nephrol., 23:163-168, 2008.

SUMMARY

The objective underlying the present invention is the provision of new medical uses for liposome compositions. Another object is the provision of new therapies for endogenous and exogenous toxicopathies, in particular drug, metabolite, pesticide, insecticide, toxin and chemical warfare toxicopathies. A further objective of the present invention is the provision of a new treatment for hyperammonemia.

The above objectives are solved by a liposome composition for use in the peritoneal dialysis of patients suffering from endogenous or exogenous toxicopathies, wherein the pH within the liposomes differs from the pH in the peritoneal cavity and wherein the pH within the liposome results in a liposome-encapsulated charged toxin.

The term "liposome composition for use in the peritoneal dialysis" is meant to refer to a liposome composition that (i) is suitable for intraperitoneal administration, i.e. it is made of physiologically acceptable lipids and further components, (ii) is stable under physiological conditions, in particular those of the peritoneal cavity and blood, for a time suitable for the uptake and prolonged retention of drugs and metabolites, and that (iii) displays a transmembrane transfer capacity.

For practicing the present invention, it is necessary that the pH within the liposomes differs from the pH in the peritoneal cavity and that the pH within the liposomes results in a liposome-encapsulated charged toxin.

In view of the above, the liposome composition of the present invention is a physiologically acceptable, stable, transmembrane, pH-gradient liposome composition suitable for peritoneal administration that is pH-adapted for the particular toxin to be charged within the liposome.

The term "peritoneal dialysis" as used herein is meant to be understood as it is commonly understood by the person skill in the art of peritoneal dialysis treatment. For practicing the invention, a pharmaceutically effective amount of the liposome composition of the invention is administered into the peritoneal cavity, e.g. by injection as a single bolus or by continuous infusion or perfusion. The liposomes within the cavity and the nearby tissues and organs will take up the toxin of interest. The pH within the liposome is adapted so that the toxin is charged upon membrane transfer, i.e. protonated or deprotonated to result in a positively or negatively charged toxin compound that cannot transfer back through the hydrophobic liposome bilayer.

The drug-entrapping liposome sequesters the toxin for a prolonged time period and reduces the toxic concentration of the free compound. The liposome can be left in the peritoneal cavity and body tissues if the toxic concentration resulting from the eventual biodegradation of the liposome and release of the toxin is not pathological to the patient. On the other hand, it is preferred that the liposome composition and/or size is adapted to prolong peritoneal localization. In that case, it is preferred that the toxin-loaded liposomes in the abdominal cavity are suction-extracted from the peritoneal cavity. Intraperitoneal administration and extraction can be performed subsequently and/or simultaneously.

Physiologically acceptable, transmembrane, pH-gradient liposome compositions suitable for practicing the present invention can be prepared as abundantly described in the prior art, for example in the documents referenced above. The liposome formulation may comprise vesicles of various nature (unilamellar, multilamellar), compositions, sizes, and characteristics, enclosing an aqueous medium of diverse compositions, pH and osmotic strength. In preferred embodiments the main constituents of the liposome lipid layer membrane are selected from the group consisting of natural or synthetic phospholipids such as those listed below:

1,2-Dilauroyl-sn-Glycero-3-Phosphocholine (DLPC)
1,2-Dimyristoyl-sn-Glycero-3-Phosphocholine (DMPC)
1,2-Dipalmitoyl-sn-Glycero-3-Phosphocholine (DPPC)
1,2-Distearoyl-sn-Glycero-3-Phosphocholine (DSPC)
1,2-Dioleoyl-sn-Glycero-3-Phosphocholine (DOPC)
1,2-Dimyristoyl-sn-Glycero-3-Phosphoelhanolamine (DMPE)
1,2-Dipalmitoyl-sn-Glycero-3-Phosphoelhanolamine (DPPE)
1,2-Distearoyl-sn-Glycero-3-Phosphoelhanolamine (DSPE)
1,2-Dioleoyl-sn-Glycero-3-Phosphoelhanolamine (DOPE)
1-Myristoyl-2-Palmitoyl-sn-Glycero-3-Phosphocholine (MPPC)
1-Palmitoyl-2-Myristoyl-sn-Glycero-3-Phosphocholine (PMPC)
1-Stearoyl-2-Palmitoyl-sn-Glycero-3-Phosphocholine (SPPC)
1-Palmitoyl-2-Stearoyl-sn-Glycero-3-Phosphocholine (PSPC)
1,2-Dimyristoyl-sn-Glycero-3-[Phospho-rac-(1-glycerol)] (DMPG)
1,2-Dipalmitoyl-sn-Glycero-3-[Phospho-rac-(1-glycerol)] (DPPG)
1,2-Distearoyl-sn-Glycero-3-[Phospho-rac-(1-glycerol)] (DSPG)
1,2-Dioleoyl-sn-Glycero-3-[Phospho-rac-(1-glycerol)] (DOPG)
1,2-Dimyristoyl-sn-Glycero-3-Phosphate (DMPA)
1,2-Dipalmitoyl-sn-Glycero-3-Phosphate (DPPA)
1,2-Dipalmitoyl-sn-Glycero-3-[Phospho-L-Serine] (DPPS)

Natural L-α-phosphatidylcholine (from chicken egg, EPC, or from soy, SPC)

Preferred phospholipids are long saturated phospholipids, e.g. those having alkyl chains of more than 12, preferably more than 14, more preferably more than 16, most preferably more than 18 carbon atoms.

Preferred liposome compositions for use according to the invention are preferably those, wherein the liposomes are uni- and/or multilamellar, and comprise
  (i) 1 to 100, preferably 40 to 70 mol % physiologically acceptable phospholipids, preferably selected from the group consisting of DLPC, DMPC, DPPC, DSPC, DOPC, DMPE, DPPE, DSPE, DOPE, MPPC, PMPC, SPPC, PSPC, DMPG, DPPG, DSPG, DOPG, DMPA, DPPA, DPPS, EPC, and/or SPC.
  (ii) 1 to 100, preferably 40 to 70 mol % sphingolipids, preferably sphingomyelin;
  (iii) 1 to 100, preferably 40 to 70 mol % surfactants, preferably featuring hydrophobic alkyl ethers (e.g. Brij), alkyl esters, polysorbates, sorbitan esters, and/or alkyl amides;
  (iv) 5 to 100, preferably 50 to 100 mol % amphiphilic polymers and/or coolymers, preferably block copolymers comprising at least one block of a hydrophilic polymer or copolymer such as polyethylene glycol, and at least one block of a hydrophobic polymer or copolymer such as poly(lactide), poly(caprolactone), poly(butylene oxide), poly(styrene oxide), poly(styrene), poly(ethylethylene), or polydimethylsiloxanes,
  (v) 0 to 60 mol %, preferably 20 to 50 mol % toxin retention-enhancing compounds, preferably sterol derivatives, preferably cholesterol,
  (vi) 0 to 30 mol %, preferably 1 to 5 mol % steric stabilizers, preferably PEGylated compounds, preferably PEGylated lipids, more preferably DSPE-PEG.

In preferred embodiments liposome-like vesicles are made from polymers and comprise no lipids, for which reason they are formally not considered liposomes and are called polymersomes. However, for the purpose of the present invention polymersomes are meant to be encompassed by the term liposome as used for defining the invention and the claims.

Similarly, liposome-like vesicles made from synthetic surfactants and comprising no lipids are called niosomes. However, for the purpose of the present invention niosomes are meant to be encompassed by the term liposome as used for defining the invention and the claims.

In a preferred embodiment the liposomes for use in the invention comprise 10 to 100, more preferably 30 to 80, more preferably 40 to 70, most preferably 50 to 60 mol % of physiologically acceptable phospholipids.

In a preferred embodiment the liposomes for use in the invention comprise 10 to 100, more preferably 25 to 75, more preferably 40 to 70, most preferably 50 to 60 mol % of sphingolipids, preferably sphingomyelin.

In a preferred embodiment the liposomes for use in the invention comprise 30 to 100, more preferably 40 to 95, most preferably 45 to 60 mol % of surfactants.

In a preferred embodiment the liposomes for use in the invention comprise 5 to 100, more preferably 30 to 100, more preferably 60 to 100, most preferably 95 to 100 mol % of amphiphilic polymers and/or copolymers.

In preferred embodiments the concentration of the sterols in the liposome composition varies between 0 and 60, preferably 20 and 50, more preferably 30 to 45 mol % for enhanced retention of the metabolite or drug.

In a further preferred embodiment the concentration of the steric stabilizer, preferably PEGylated lipids, in the liposome composition varies between 0 and 30, preferably 0.5 and 20, more preferably 1 to 5 mol %.

In another preferred embodiment the diameter size of the liposomes is larger than 600, preferably larger than 700, most preferably larger than 800 nm, i.e. a diameter size of 600 nm to 10 µm, preferably 700 nm to 10 µm, more preferably 800 nm to 5 µm to avoid too rapid drainage from the peritoneal space.

The aqueous solution within the lipid bilayer of the liposome of the invention is preferably isotonic, preferably has a high buffering capacity at low pH (e.g. citrate, sulfate, acetate, benzoate, formate, glycolate, malate buffer) for a high retention of basic compounds and a high buffering capacity at high pH (e.g. calcium acetate, bis-tris propane, sulfonates (CAPS, CABS, TABS, CHES), bicine, tricin, ethanolamine buffer) for a high retention of acidic compounds. The pH and buffering compounds have to be adapted to the toxin of interest. For example, ammonium sulfate, i.e. a weak base, would not be suitable for scavenging the strong base ammonia (i.e. treatment of hyperammonemia), because it would introduce ammonia into the body, a compound which is aimed at being eliminated. For the sequestration of weak acids, the internal aqueous solution should be a basic buffer (e.g. calcium acetate).

Preferably, the liposome composition of the invention features a pH within the liposome composition of 1 to 6.5, preferably 1.5 to 5, more preferably 1.5 to 4.

Also preferred is that the liposome composition for use in the invention features a pH within the liposome composition of 8.5 to 12, preferably 9 to 11, more preferably 9 to 10.

In a most preferred embodiment, the liposome composition for use in the invention is one wherein the liposome bilayer comprises:
  (i) 50 to 60, preferably about 54 mol % DPPC,
  (ii) 40 to 50, preferably 45 mol % cholesterol (CHOL), and 0.5 to 2, preferably 1 mol % 1,2-distearoyl-sn-glycero-3-phosphoethanolamine-N-[methoxy(polyethylene glycol)-2000] (DSPE-PEG),
  and the aqueous solution within the liposomes comprises 250 mM citrate solution buffered at pH 1.5 to 3, preferably 2,
  and wherein the diameter of the liposomes is 800 nm or larger, preferably 900 nm or larger, more preferably 1000 nm or larger.

The above liposome composition is preferred for treating hyperammonemia.

Further examples of liposomes suitable for practicing the invention are (in molar ratios): DMPC/CHOL, 2:1; DPPC/CHOL, 2:1; DSPC:CHOL, 2:1; DSPC/CHOL/PEG-2000-DSPE, 2:1:0,2; DSPC/DSPG/CHOL, 60:10:30; DSPC/DSPG/CHOL/PEG2000-DSPE, 55.83:10:27.92:6.25, EPC/CHOL/DESP-PEG, 50:45:5, sphingomyelin/DPPC/CHOL/DSPE-PEG, 25:25:45:5, comprising and internal buffer of citrate 110 mM pH 4, or 200 mM pH 3, or 250 mM pH 3, or 250 mM pH 2, or 300 mM pH 2.

The terms exogenous and endogenous toxicopathy indicate the involvement of a toxin produced by the body, i.e. endogenous toxin, or a toxin introduced from externally into the body, i.e. exogenous toxin.

Preferably, the liposome composition of the invention is for treating an exogenous toxicopathy selected from the group consisting of metabolite, drug, pesticide, insecticide, toxin and chemical warfare toxicopathies. Preferred herbicide intoxications are from auxins or atrazine and a preferred pesticide intoxication is from neonicotinoid.

In a preferred embodiment, the present invention is directed to the treatment of a metabolite toxicopathy. The term "metabolite toxicopathy" as used herein is meant to indicate a toxic concentration of endogenous compounds leading to pathological conditions, e.g. ammonia, argininosuccinate, uric acid, isovaleric acid, propionic acid. The term does not include pathologies based on exogenous metabolites, e.g. drug metabolites.

Preferred metabolite toxicopathies are selected from the group consisting of hyperammonemia, argininosuccinic acidemia, hyperuricemia, isovaleric acidemia and propionic acidemia.

In a further preferred embodiment, the present invention is directed to the treatment of a drug toxicopathy, preferably selected from the group consisting of acidic and basic drugs.

Drugs suitable for intraperitoneal liposome entrapment according to the invention are preferably selected from the group consisting of (1) antineoplastics, preferably selected from the group consisting of mitoxantrone, epirubicin, daunorubicin, doxorubicin, ciprofloxacin, vincristine, vinorelbine, or vinblastine;
(2) local anesthetics, preferably selected from procaine, lidocaine, bupivacaine, chlorpromazine, midazolam or dibucaine;
(3) adrenergic antagonists, preferably propranolol, phenylephrine, alprenolol, atenolol, clenbuterol, salbutamol or timolol;
(4) antiarrythmetic agents, preferably quinidine;
(5) cholinergic agents, preferably pilocarpine or physostigmine;
(6) antidepressants, preferably imipramine, nortriptyline, amitriptyline, bupropion, doxepine, or venlafaxine;
(7) antihistamines, preferably diphenylhydramine, or chlorphenamine;
(8) antimalarial agents, preferably primaquine, quinine, chloroquine, amodiaquine, or pyrimethamine;
(9) antiprotozoan agents, preferably quinacrine;
(10) analgesics, preferably codeine, acetaminophen, aspirin, fentanyl, methadone, or pethidine;
(11) cardiovascular drugs, preferably diltiazem, verapamil, or dipyridamole;
(12) anticonvulsants, preferably valproic acid, or phenobarbital;
(13) antipsychotic drugs, preferably quetiapine, chlorpromazine or haloperidol;
(14) anti-anxiety drugs, preferably alprazolam, or diazepam;
(15) anti-inflammatory drugs, preferably diclofenac, or ibuprofen;
(16) erectile dysfunction drugs, preferably sildenafil, or tadalafil;
(17) anti-tuberculosis drugs, preferably ethambutol, isoniazid, or pyrazinamide;
(18) neurotransmitters, preferably epinephrine, or norepinephrine;
(19) psychostimulants, preferably amphetamine, MDMA, methylphenidate, cocaine, or heroin.

Most preferred drugs involved in intoxications that can be treated with liposome compositions for peritoneal dialysis of the present invention are:

Acetylsalicylic acid, Alprazolam, Amitriptyline, Amlodipine, Amphetamine, Atenolol, Atropine, Bupivacaine, Bupropion, Captopril, Chloroquine, Chlorpheniramine, Chlorpromazine, Chlorpropamide, Clenbuterol, Cocaine, Codeine, Diazepam, Diltiazem, Diphenhydramine, Dipyridamole, Disopyramide, Doxepine, Ethambutol, Fentanyl, Fentanyl, Haloperidol, Heroin, Ibuprofen, Imipramine, Isoniazid, Ketoprofen, Lidocaine, Lorazepam, MDMA, Metformin, Methadone, Methadone, Methylphenidate, Nifedipine, Nortriptyline, Pethidine, Phenobarbital, Phenprocoumon, Procainamide, Propranolol, Pyrimethamine, Quetiapine, Quinacrine, Quinidine, Quinine, Ropivacaine, Sildenafil, Valproic acid, Venlafaxine, Verapamil, Warfarin.

The liposome compositions of the invention are preferably used for treating human patients suffering from endogenous or exogenous toxicopathies. Also preferred is the use of liposome compositions for treating mammals and birds, preferably mammals selected from the group consisting of swine, cattle, dog, cat, sheep, goat and horse, etc. suffering from endogenous or exogenous toxicopathies.

A further aspect of the present invention relates to a pharmaceutical composition comprising at least one liposome composition of the invention and optionally one or more pharmaceutically acceptable excipients. Pharmaceutical compositions of the present invention typically comprise a therapeutically effective amount of a liposome composition according to the invention and optionally auxiliary substances such as pharmaceutically acceptable excipient(s). Said pharmaceutical compositions are prepared in a manner well known in the pharmaceutical art. A carrier or excipient may be a liquid material which can serve as a vehicle or medium for the active ingredient. Suitable carriers or excipients are well known in the art and include, for example, stabilizers, suspending agents, osmotic agents (such as glucose solutions, gelatin, xylitol, sorbitol, mannitol, glucose polymer (e.g, icodextrin), or amino acids), antimicrobial preservatives, antioxidants, pH-regulating substances (e.g. sodium and potassium lactate), coloring agents, etc. The pharmaceutical preparation of the invention must be suitable for intraperitoneal administration and may be administered to the patient, preferably a human, in the form of solutions, suspensions, or the like.

Another aspect of the present invention concerns a method of treatment, i.e. a method of treating patients suffering from endogenous or exogenous toxicopathies, comprising the step of administering a liposome composition according to the invention in a therapeutically effective amount into the peritoneal space of a patient in need thereof.

Preferably, the exogenous toxicopathy to be treated is selected from the group consisting of drug, pesticide, insecticide, toxin and chemical warfare toxicopathies. Also preferred is that the metabolite toxicopathy to be treated is selected from the group consisting of hyperammonemia, argininosuccinic acidemia, hyperuricemia, isovaleric acidemia and propionic acidemia.

Preferably, the patients for being treated according to the invention are humans.

In an alternative embodiment of the method of the invention the patients suffering from endogenous or exogenous toxicopathies are selected from mammals and birds, preferably mammals selected from the group consisting of swine, cattle, dog, cat, sheep, goat, and horse, etc.

In effecting treatment of patients suffering from endogenous or exogenous toxicopathies as described above, a liposome composition of the present invention can be administered in any form or mode which makes the liposomes or liposome-like vesicles, e.g. polymersomes or niosomes, bioavailable in an effective amount within the peritoneal cavity. Preferably intraperitoneal liposome administration is by bolus injection, infusion and/or perfusion. One skilled in the art in the field of preparing intraperitoneal formulations can readily select the proper form and mode of administration depending upon the particular characteristics of the toxin to be sequestered and/or removed.

In a preferred embodiment the method of the invention further comprises the step of extracting the liposomes from the abdominal cavity either subsequently to and/or simultaneously to the administration step.

In the following, the invention will be illustrated with reference to specific experimental embodiments and figures, none of which are intended to limit the invention beyond the scope of the appended claims.

DETAILED DESCRIPTION

Examples

Figure 1:
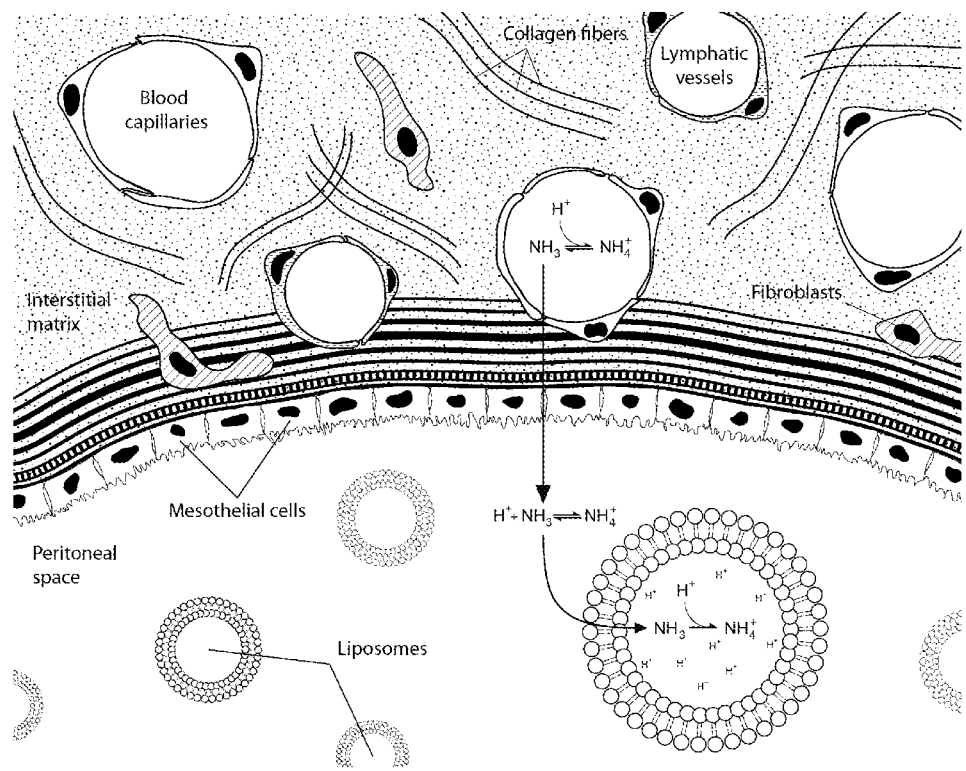
FIG. 1 illustrates the sequestration of toxic substances (e.g. drugs or ammonia, $NH_3$) in the peritoneal space by transmembrane pH-gradient liposomes (case of a weak base). The unionized compound diffuses from the blood capillaries to the peritoneal space, where it gets trapped in an ionized form ($NH_4^+$) in the vesicles. Diffusion continues until the liposomes internal buffering capacity is overwhelmed.
Figure 2:
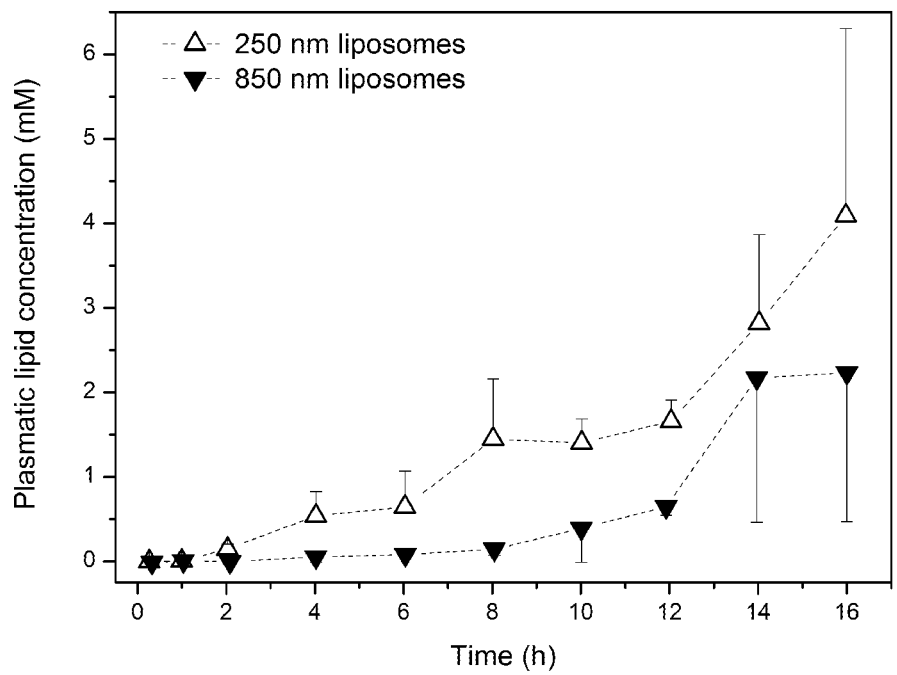
FIG. 2 is a graph illustrating the liposomes drainage from the peritoneal space to the blood after intraperitoneal administration. A non-exchangeable sterol dye (Cholesteryl BODIPY® FL-C12, Invitrogen) was incorporated (0.05 mol %) in the liposomal membrane (during the lipid film production process). After intraperitoneal administration of liposomes, the dye fluorescence ($\lambda_{ex}$=470 nm, $\lambda_{em}$=520 nm) was measured in the plasma aliquots and compared to a calibration curve to obtain the liposomal lipid concentration. Larger liposomes remained longer (8 h) in the peritoneal space whereas small liposomes were found in blood at important concentrations after 4 h. Mean±SD (n=3).
Figure 3:
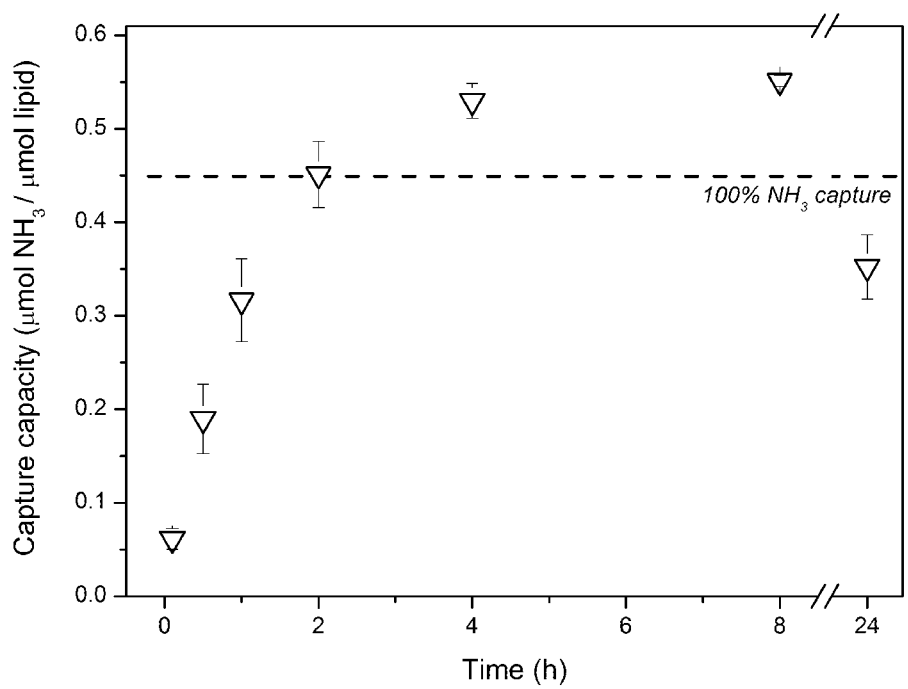
FIG. 3. is a graph showing the in vitro ammonia uptake by pH-gradient liposomes in 50% fetal bovine serum at 37° C. Liposomes exhibited a rapid and efficient uptake of ammonia. The initial ammonia and liposome concentrations were set at 1.7 and 3.8 mM, potentially tolerating a maximal capture capacity of 0.45 µmol ammonia/µmol lipid. Interestingly, the vesicles sequestered more than the total amount of ammonia loaded in the system (dashed line). The surplus came from the native ammonia present in the serum. The liposome diameter was of 840 nm Mean±SD (n=6).
Figure 4:
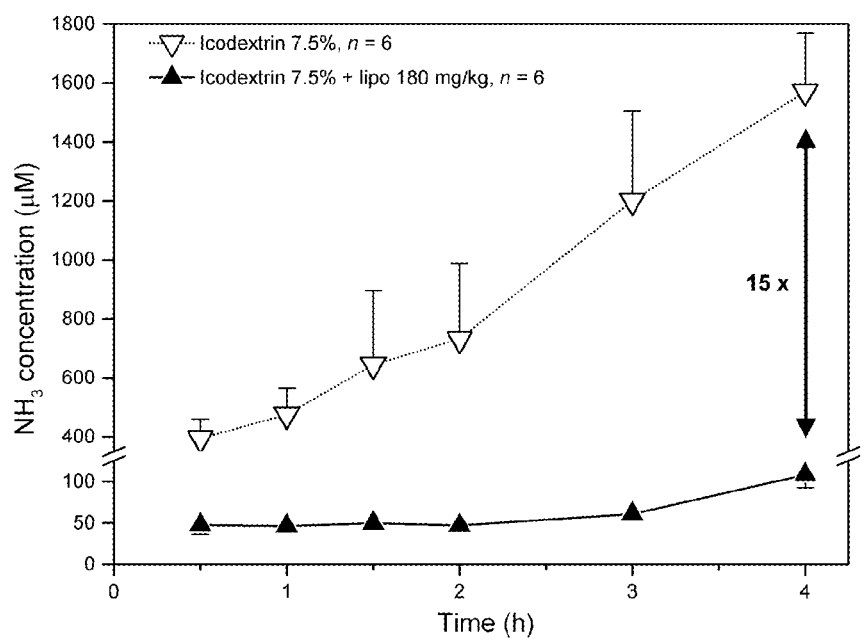
FIG. 4 is a graph showing the concentration of ammonia ($NH_3$) in peritoneal dialysate in the absence (closed triangles) and presence (open triangles) of liposomes. The dialysis fluid was injected intraperitoneally at t=0 h in healthy rats. The injected liposome dose was 180 mg/kg, and the lipid concentration in the dialysis fluid was of 15 mM. The liposome diameter was of 850 nm.
Figure 5:
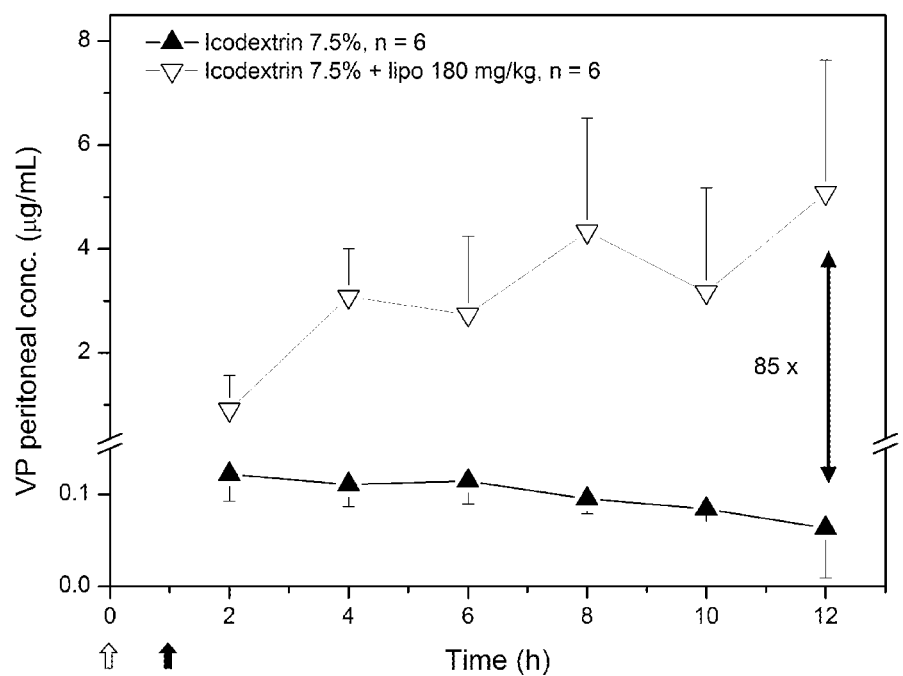
FIG. 5 is a graph showing the concentration of verapamil (VP) in peritoneal dialysate in the absence (closed triangles) and presence (open triangles) of liposomes. VP was administered by oral gavage at t=0 h (50 mg/kg, ⇧), followed by the intraperitoneal injection of the dialysis fluid at t=1 h with (♦). The injected liposome dose was 180 mg/kg, and the lipid concentration in the dialysis fluid was of 15 mM. The liposome diameter was of 850 nm.

In the following examples it was demonstrated that an illustrative liposome composition (Example 1) can be retained for a prolonged time period in the peritoneal space after intraperoneal administration depending on the size of the liposomes (Example 2). These liposomes exhibited a rapid and efficient uptake of ammonia in 50% fetal bovine serum (Example 3). Moreover, these liposomes were capable of entrapping and concentrating ammonia (Example 4) and orally administered drug verapamil (Example 5) in the peritoneal space, thus demonstrating the utility of such liposomes for the detoxification of metabolites and drugs by intraperitoneal administration.

Example 1—Liposome Composition and Preparation

The formulation tested in the following experiments in vivo was composed of DPPC with 45 mol % of CHOL and 5 mol % of DSPE-PEG. The aqueous solution within the liposomes was a 250 mM sodium citrate solution buffered at pH 2. The formulations were prepared by the lipid film hydration/extrusion method (Hope M, Bally M, Webb G, Cullis PR. Production of large unilamellar vesicles by a rapid extrusion procedure. Characterization of size distribution, trapped volume and ability to maintain a membrane potential. Biochim Biophys Acta 1985, 55-65). Lipids, CHOL, and eventually the Cholesteryl BODIPY® FL-C12 dye, from Invitrogen (0.05 mol %) were dissolved in chloroform which was subsequently removed under continuous nitrogen flow and high vacuum for >12 h. The lipid film was hydrated with citrate buffer (250 mM, pH 2). The large vesicles were obtained by extrusion through 2 stacked membranes of 5 µm. The transmembrane pH-gradient was established by dialysis in normal saline for >12 h (membrane cut-off: 1000 kDa).

Example 2—Liposomes Drainage from the Peritoneal Space to the Blood after Intraperitoneal Administration Sprague-dawley rats (male, 300 g) were lightly anesthetized by isofluran inhalation (2%) and 20 mL of a solution of icodextrin 7.5% containing liposomes (either 250 or 850 nm of diameter) bearing the non-exchangeable sterol dye (Cholesteryl BODIPY® FL-C12, Invitrogen, 0.05 mol %) in their membrane were slowly injected in the peritoneal space through sterile puncture. Then, blood aliquots of 250 uL were sampled through the tail veins at 15 min, 1, 2, 4, 6, 8, 10, 12, 14, 16 h after i.p. injection. Plasma was separated from the blood aliquots by centrifugation (6000 g for 10 min) and the dye fluorescence measured in plasma at $\lambda_{em}$=520 nm ($\lambda_{ex}$=470 nm).

Example 3—In Vitro Ammonia Uptake by pH-Gradient Liposomes in 50% Fetal Bovine Serum Ammonia ($NH_3$) uptake kinetics were monitored in 50% FBS in side-by-side diffusion cells (PermGear, Hellertown, Pa.) at 37° C. The liposomes used in this experiment had a diameter of 850 nm and contained 54 mol % DPPC, 45 mol % of cholesterol, and 1 mol % of DSPE-PEG, and an internal citrate solution (250 mM) buffered at pH 2. The donor compartment (liposome-free) was separated from the receiver compartment (containing liposomes) by a polycarbonate membrane with 100 nm pores. The $NH_3$-to-lipid molar ratio was set to 0.45 with an initial $NH_3$ concentration of 1.7 mM in both cells to achieve equilibrium. $NH_3$ uptake by the vesicles in the receiver compartment was directly related to the reduction of toxin concentration in the donor cell. Aliquots of 100 μL were sampled from the donor compartment 3, 30 min, 1, 2, 4, 8, and 24 h after injection of pH-gradient liposomes in the receiver compartment. $NH_3$ was then quantified by a colorimetric assay (Berthelot MPE, Violet d'aniline Repert Chim Appl 1859, 1:284).

Example 4—Concentration of Ammonia in Peritoneal Dialysate in the Absence and Presence of Liposomes Sprague-Dawley rats (300 g) were lightly anesthetized with isoflurane (2.5%, 0.6 L/min O2), kept on a warming blanket, and 20 mL of a solution of icodextrin 7.5% with (or without) liposomes (3 mg/mL) was slowly infused in the peritoneal space through sterile abdominal puncture with a 22 G silicon catheter (Venflon; Becton Dickinson). The liposomes used in this experiment had a diameter of 850 nm and contained 54 mol % DPPC, 45 mol % of cholesterol, and 1 mol % of DSPE-PEG, and an internal citrate solution (250 mM) buffered at pH 2. Aliquots of peritoneal dialysate were sampled 0.5, 1, 1.5, 2, 3, and 4 h after dialysis onset. The ammonia content in peritoneal fluid samples was assayed by a colorimetric assay (Berthelot MPE, Violet d'aniline. Repert Chim Appl 1859, 1:284).

Example 5—Concentration of Verapamil in Peritoneal Dialysate in the Absence and Presence of Liposomes One hour after administration of verapamil (50 mg/kg, p.o.) to Sprague-Dawley rats (300 g), animals were lightly anesthetized with isoflurane (2.5%, 0.6 L/min $O_2$), kept on a warming blanket, and 20 mL of a solution of icodextrin 7.5% with (or without) liposomes (3 mg/mL) was slowly infused in the peritoneal space through sterile abdominal puncture with a 22 G silicon catheter (Venflon; Becton Dickinson). The liposomes used in this experiment had a diameter of 850 nm and contained 54 mol % DPPC, 45 mol % of cholesterol, and 1 mol % of DSPE-PEG, and an internal citrate solution (250 mM) buffered at pH 2. Aliquots of peritoneal dialysate were sampled 2, 4, 6, 8, 10, and 12 h after the oral gavage of verapamil. The drug content peritoneal fluids was assayed by HPLC, as described in, e.g. Forster et al., Biomaterials 33, 3578-3585, 2012).

The invention claimed is:
1. A method for removing endogenous or exogenous toxins from a patient in need thereof by peritoneal dialysis comprising:
    (a) the step of administering a therapeutically effective amount of a liposome composition into the peritoneal cavity of said patient, wherein the pH within the liposomes differs from the pH in the peritoneal cavity, wherein the pH within the liposomes results in a liposome-encapsulated charged toxin, and wherein the diameter size of the liposomes in the liposome composition is larger than 600 nm; and
    (b) the step of subsequently extracting the dialysate containing the liposome-encapsulated toxin.
2. The method according to claim 1, wherein the diameter size of the liposomes in the liposome composition is selected from the diameter size ranges of 600 nm to 10 μm, 700 nm to 10 μm, and 800 nm to 5 μm.
3. The method according to claim 1, wherein the pH within the liposome composition is 1 to 6.5.
4. The method according to claim 3, wherein the pH within the liposome composition is 1.5 to 4.
5. The method according to claim 1, wherein the pH within the liposome composition is 8.5 to 12.
6. The method according to claim 5, wherein the pH within the liposome composition is 9 to 10.
7. The method according to claim 1, wherein the liposomes in the liposome composition are uni- and/or multilamellar, and comprise at least one of:
    (i) 1 to 100 mol % physiologically acceptable phospholipids;
    (ii) 1 to 99 mol % sphingolipids;
    (iii) 1 to 99 mol % surfactants;
    (iv) at least 5 mol % amphiphilic polymers and/or copolymers;
    (v) 0 to 60 mol % toxin retention-enhancing compounds; or
    (vi) 0 to 30 mol % steric stabilizers.
8. The method according to claim 7, wherein the physiologically acceptable phospholipids are selected from the group consisting of DLPC, DMPC, DPPC, DSPC, DOPC, DMPE, DPPE, DSPE, DOPE, MPPC, PMPC, SPPC, PSPC, DMPG, DPPG, DSPG, DOPG, DMPA, DPPA, DPPS, EPC, and SPC.
9. The method according to claim 7, wherein the sphingolipids comprise sphingomyelin.
10. The method according to claim 7, wherein the surfactants are selected from the group consisting of hydrophobic alkyl ethers, alkyl esters, polysorbates, spans, and alkyl amides.
11. The method according to claim 7, wherein the amphiphilic polymers and/or copolymers are selected from the group consisting of block copolymers comprising at least one block of a hydrophilic polymer or copolymer, and at least one block of a hydrophobic polymer or copolymer.
12. The method according to claim 7, wherein the toxin retention-enhancing compounds are selected from the group consisting of cholesterol and sterol derivatives.
13. The method according to claim 7, wherein the steric stabilizers are selected from the group consisting of PEGylated compounds (PEG, polyethylene glycol), PEGylated lipids, and DSPE-PEG.
14. The method according to claim 1, wherein the bilayer of the liposomes comprises:
    (i) 50 to 60 mol % 1,2-dipalmitoyl-sn-glycero-3-phosphocholine (DPPC),
    (ii) 40 to 50 mol % cholesterol (CHOL), and
    (iii) 0.5 to 2 mol % 1,2-distearoyl-sn-glycero-3-phosphoethanolamine-N-[methoxy(polyethylene glycol)-2000] (DSPE-PEG), wherein the aqueous solution within the liposomes comprises 250 mM citrate solution buffered at pH 1.5 to 3, and wherein the diameter of the liposomes is 800 nm or larger.
15. The method according to claim 1, wherein the exogenous toxin is selected from the group consisting of drugs, pesticides, insecticides and chemical warfare toxins.
16. The method according to claim 15, wherein the exogenous drug toxin is selected from the group consisting of acidic and basic drugs.
17. The method according to claim 16, wherein the acidic or basic drugs are selected from the group consisting of:
    (1) antineoplastics;
    (2) local anaesthetics;
    (3) adrenergic antagonists;
    (4) antiarrythmetic agents;
    (5) cholinergic agents;
    (6) antidepressants;
    (7) antihistamines;
    (8) antimalarial agents;

(9) antiprotozoan agents;
(10) analgesics;
(11) cardiovascular drugs;
(12) anticonvulsants;
(13) antipsychotic drugs;
(14) anti-anxiety drugs;
(15) anti-inflammatory drugs;
(16) erectile dysfunction drugs;
(17) anti-tuberculosis drugs;
(18) neurotransmitters; and
(19) psychostimulants.

18. The method according to claim 1, wherein the endogenous toxin is selected from the group consisting of ammonia, argininosuccinate, uric acid, isovaleric acid and propionic acid.

19. The method according to claim 1, wherein the patients in need thereof are humans.

20. The method according to claim 1, wherein the patients in need thereof are selected from the group consisting of swine, cattle, dogs, cats, sheep, goats, horses and birds.

21. The method according to claim 1, wherein the liposomes are polymersomes or niosomes.

22. The method according to claim 1, wherein the step of administering the therapeutically effective amount of the liposome composition into the peritoneal cavity of the patient in need thereof is by bolus injection, infusion and/or perfusion.

23. The method according to claim 11, wherein the block copolymer comprising at least one block of a hydrophilic polymer or copolymer is polyethylene glycol.

24. The method according to claim 11, wherein the block of a hydrophobic polymer or copolymer is selected from the group consisting of poly(lactide), poly(caprolactone), poly(butylene oxide), poly(styrene oxide), poly(styrene), poly(ethylethylene), and polydimethylsiloxanes.

25. The method according to claim 17, wherein:
   (1) the antineoplastics are selected from the group consisting of mitoxantrone, epirubicin, daunorubicin, doxorubicin, ciprofloxacin, vincristine, vinorelbine, and vinblastine;
   (2) the local anaesthetics are selected from the group consisting of procaine, lidocaine, bupivacaine, chlorpromazine, midazolam, and dibucaine;
   (3) the adrenergic antagonists are selected from the group consisting of propranolol, phenylephrine, alprenolol, atenolol, clenbuterol, salbutamol, and timolol;
   (4) the antiarrythmetic agent is quinidine;
   (5) the cholinergic agents are selected from the group consisting of pilocarpine and physostigmine;
   (6) the antidepressants are selected from the group consisting of imipramine, nortriptyline, amitriptyline, bupropion, doxepine, and venlafaxine;
   (7) the antihistamines are selected from the group consisting of diphenylhydramine and chlorphenamine;
   (8) the antimalarial agents are selected from the group consisting of primaquine, quinine, chloroquine, amodiaquine, and pyrimethamine;
   (9) the antiprotozoan agent is quinacrine;
   (10) the analgesics are selected from the group consisting of codeine, acetaminophen, aspirin, fentanyl, methadone, and pethidine;
   (11) the cardiovascular drugs are selected from the group consisting of diltiazem, verapamil, and dipyridamole;
   (12) the anticonvulsants are selected from the group consisting of valproic acid and phenobarbital;
   (13) the antipsychotic drugs are selected from the group consisting of quetiapine, chlorpromazine, and haloperidol;
   (14) the anti-anxiety drugs are selected from the group consisting of alprazolam and diazepam;
   (15) the anti-inflammatory drugs are selected from the group consisting of diclofenac and ibuprofen;
   (16) the erectile dysfunction drugs are selected from the group consisting of sildenafil and tadalafil;
   (17) the anti-tuberculosis drugs are selected from the group consisting of ethambutol, isoniazid, and pyrazinamide;
   (18) the neurotransmitters are selected from the group consisting of epinephrine and norepinephrine; and
   (19) the psychostimulants are selected from the group consisting of amphetamine, MDMA, methylphenidate, cocaine, and heroin.

26. The method according to claim 7, wherein the physiologically acceptable phospholipid is DPPC, the toxin retention-enhancing compound is cholesterol, and the steric stabilizer is DSPE-PEG.

27. The method according to claim 1, wherein the bilayer of the liposome comprises:
   (i) 1 to 100 mol % of DPPC;
   (ii) 0 to 60 mol % of cholesterol; and
   (iii) 0 to 30 mol % of DSPE-PEG.

28. The method according to claim 27, wherein the bilayer of the liposome comprises:
   (i) 10 to 100 mol % of DPPC;
   (ii) 0 to 60 mol % of cholesterol; and
   (iii) 0.5 to 2% mol % of DSPE-PEG.

* * * * *

UNITED STATES PATENT AND TRADEMARK OFFICE
CERTIFICATE OF CORRECTION

PATENT NO. : 10,596,114 B2
APPLICATION NO. : 14/420654
DATED : March 24, 2020
INVENTOR(S) : Leroux et al.

Page 1 of 2

It is certified that error appears in the above-identified patent and that said Letters Patent is hereby corrected as shown below:

In the Drawings

Please replace Figures 3 and 4 with replacement Figures 3 and 4. (Attached)

In the Claims

In Column 11, Claim 3, Line 65, "liposome composition" should read "liposomes".
In Column 11, Claim 4, Line 67, "liposome composition" should read "liposomes".
In Column 12, Claim 5, Line 2, "liposome composition" should read "liposomes".
In Column 12, Claim 6, Line 4, "liposome composition" should read "liposomes".

Signed and Sealed this
Fourteenth Day of July, 2020

Andrei Iancu
*Director of the United States Patent and Trademark Office*

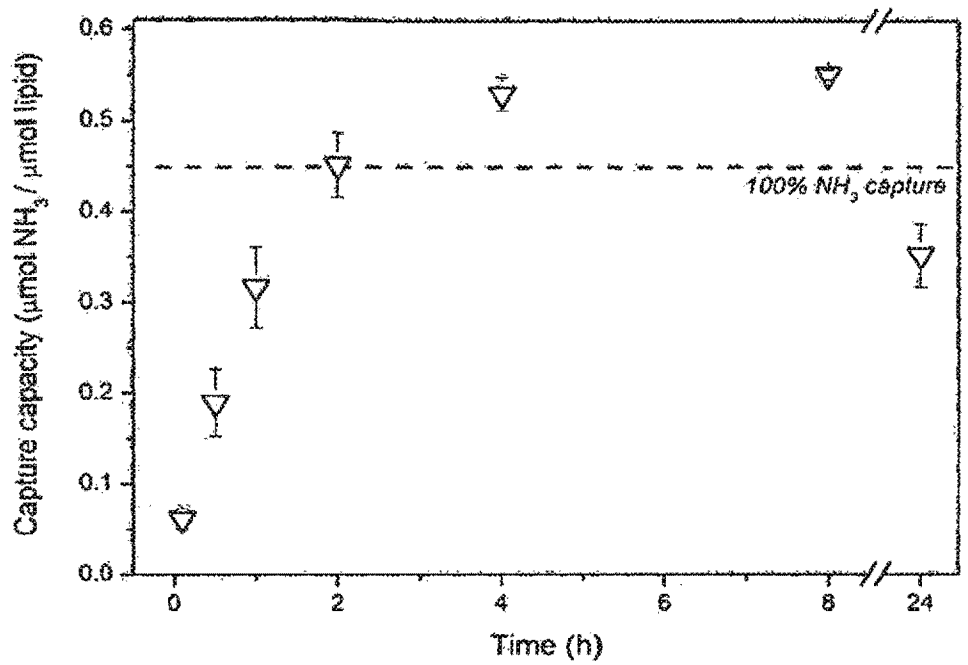
Fig. 3
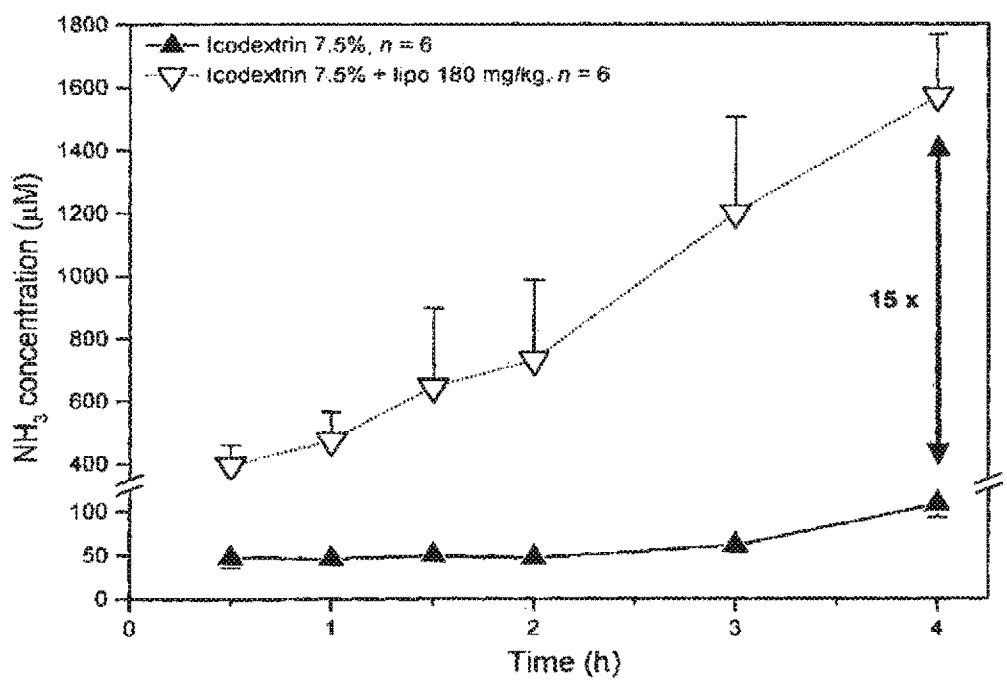
Fig. 4